& Birch, LLP

(12) United States Patent
Wang et al.

(10) Patent No.: US 7,619,726 B2
(45) Date of Patent: Nov. 17, 2009

(54) METHOD OF MEASURING LIGHT LEAKAGE INTENSITY RATIO AND FILTER

(75) Inventors: Shiao-Wen Wang, Hsin-Chu (TW);
Sheng-Wen Cheng, Hsin-Chu (TW);
Chen-Hsien Liao, Hsin-Chu (TW)

(73) Assignee: AU Optronics Corp., Hsinchu (TW)

( * ) Notice: Subject to any disclaimer, the term of this patent is extended or adjusted under 35 U.S.C. 154(b) by 320 days.

(21) Appl. No.: 11/878,565

(22) Filed: Jul. 25, 2007

(65) Prior Publication Data

US 2008/0239286 A1 Oct. 2, 2008

(30) Foreign Application Priority Data

Mar. 26, 2007 (TW) .............................. 96110336 A (51) Int. Cl.
*G02F 1/1335* (2006.01)
(52) U.S. Cl. ...................... 356/213; 356/416; 356/124; 349/57; 349/106; 349/119
(58) Field of Classification Search ........................ None
See application file for complete search history.

(56) References Cited

U.S. PATENT DOCUMENTS 6,359,671 B1 * 3/2002 Abileah ...................... 349/119

* cited by examiner

*Primary Examiner*—Gregory J Toatley, Jr.
*Assistant Examiner*—Rebecca C Slomski
(74) *Attorney, Agent, or Firm*—Birch, Stewart, Kolasch & Birch, LLP (57) ABSTRACT

A color filter with low color shift is defined by a light leakage spectrum in the dark state. The color filter is disposed between two polarizing plates so as to measure a first spectrum of dark state $a(\lambda)$, wherein the polarizing directions of the polarizers are orthogonal to each other. A second spectrum of dark state $b(\lambda)$ while the color filter is removed, and then a ratio spectrum of light leakage intensity $I(\lambda)=(a(\lambda)/b(\lambda))$ is determined. A maximum value $P_1$ in the ratio spectrum of light leakage intensity is determined in a wavelength region in which the ratio spectrum of light leakage intensity of green photoresist overlaps that of a blue photoresist. A maximum value $P_2$ in the ratio spectrum of light leakage intensity is determined in a wavelength region in which the ratio spectrum of light leakage intensity of red photoresist locates. An average value $P_{1,avg}$ of several ratios of light leakage intensity around the value $P_1$, and an average value $P_{2,avg}$ of several ratios of light leakage intensity around the value $P_2$ are determined. The color filter with low color shift meets the following formula $0.74 \leq P_{1,avg}/P_{2,avg} \leq 2$.

19 Claims, 8 Drawing Sheets

| Color Filter | Bright State | | | Dark State | | | Contrast Ratio | Chromaticity radius in dark state | Maximum P1 (N1=N2=5) | Maximum P2 (N1=N2=5) | P1avg/P2avg (N1=N2=5) |
|---|---|---|---|---|---|---|---|---|---|---|---|
| | Lv | x | y | Lv | x | y | | | | | |
| A | 392 | 0.343 | 0.367 | 0.130 | 0.326 | 0.285 | 3015 | 0.08 | 2.01 | 1.42 | 1.46 |
| B | 458 | 0.345 | 0.362 | 0.132 | 0.325 | 0.231 | 3471 | 0.13 | 1.34 | 1.88 | 0.74 |
| C | 441 | 0.357 | 0.384 | 0.091 | 0.298 | 0.259 | 4854 | 0.14 | 1.70 | 0.81 | 2.23 |
| D | 511 | 0.351 | 0.372 | 0.086 | 0.265 | 0.245 | 5913 | 0.15 | 2.53 | 0.79 | 3.22 |
| E | 487 | 0.356 | 0.381 | 0.080 | 0.292 | 0.285 | 6082 | 0.12 | 1.41 | 0.96 | 1.52 |
| F | 395 | 0.340 | 0.363 | 0.065 | 0.323 | 0.276 | 6096 | 0.09 | 0.95 | 1.14 | 0.81 |
| G | 423 | 0.349 | 0.379 | 0.049 | 0.298 | 0.296 | 8695 | 0.10 | 0.90 | 0.60 | 1.70 |
| H | 539 | 0.341 | 0.366 | 0.058 | 0.282 | 0.263 | 9272 | 0.12 | 0.85 | 0.58 | 1.69 |

Table. 1

| Color Filter | Bright State | | | Dark State | | | Contrast Ratio | Chromaticity radius in dark state | Maximum P1 (N1≠N2) | Maximum P2 (N1≠N2) | P1avg/P2avg (N1≠N2) |
|---|---|---|---|---|---|---|---|---|---|---|---|
| | Lv | x | y | Lv | x | y | | | | | |
| A | 392 | 0.343 | 0.367 | 0.130 | 0.326 | 0.285 | 3015 | 0.08 | 2.01 | 1.42 | 1.50 |
| B | 458 | 0.345 | 0.362 | 0.132 | 0.325 | 0.231 | 3471 | 0.13 | 1.34 | 1.88 | 0.76 |
| C | 441 | 0.357 | 0.384 | 0.091 | 0.298 | 0.259 | 4854 | 0.14 | 1.70 | 0.81 | 2.29 |
| D | 511 | 0.351 | 0.372 | 0.086 | 0.265 | 0.245 | 5913 | 0.15 | 2.53 | 0.79 | 3.31 |
| E | 487 | 0.356 | 0.381 | 0.080 | 0.292 | 0.285 | 6082 | 0.12 | 1.41 | 0.96 | 1.57 |
| F | 395 | 0.340 | 0.363 | 0.065 | 0.323 | 0.276 | 6096 | 0.09 | 0.95 | 1.14 | 0.88 |
| G | 423 | 0.349 | 0.379 | 0.019 | 0.298 | 0.296 | 8695 | 0.10 | 0.90 | 0.60 | 1.73 |
| H | 539 | 0.341 | 0.366 | 0.058 | 0.282 | 0.263 | 9272 | 0.12 | 0.85 | 0.58 | 1.71 |

Table. 2

METHOD OF MEASURING LIGHT LEAKAGE INTENSITY RATIO AND FILTER

BACKGROUND OF THE INVENTION (1) Field of the Invention

The invention relates to a color filter and testing method thereof, and particularly the color filter with features of low color shift and high contrast ratio.

(2) Description of the Prior Art

Following the advancement of display technology, compared to conventional CRT display, TFT-LCD (thin film transistor liquid crystal display) has become the main product because of the advantages of light, thin, low radiation and small size. Due to the rapid development of LCD products, manufacturers gets harder and harder competition.

A color filter (CF) is one of the most important components for LCD to display the color image. LCD uses liquid crystal molecules under different voltages to affect the polarized light to control gray level, and uses color filters to mix colors for different gray levels.

Color filters are usually manufactured by dispersing pigments. Under zero gray level, part-depolarization occurs because the pigment molecules affect polarized light which goes through the color filter. When polarized light goes through the upper polarizer, the polarizer has no way to absorb the polarized light completely so that a light leakage occurs.

However, different color pigments (red, blue and green) cause different levels of light leakage due to different particle sizes, so that color shift occurs in the dark state.

Generally, color filter manufactures regulate the proportion of the contrast ratios of red, blue and green photoresists for the requirement of lower color shift. However, the contrast ratio is required to increase with rising the image quality of LCD. It is very difficult to satisfy the requirement of low color shift under high contrast ratio.

In other words, above regulation of proportions is only applied to non-high contrast ratio. Under high contrast ratio, it cannot reduce the color shift.

Therefore, it is necessary to find some conditions for color filter to reduce color shift regardless of under high or low contrast ratios.

SUMMARY OF THE INVENTION

One object of this invention is to provide a light leakage spectrum of the dark state to define the conditions for the requirement of low color shift.

Another object of this invention is to overcome the color shift in dark state by defining the conditions of light leakage spectrum in the dark state for color filters. The conditions can be applied to all color filters with high or low contrast ratios.

The other object of the invention is to provide the determination conditions of light leakage spectrum for color filters in dark state to select a color filter with features of low color shift and high contrast ratio.

The invention provides a color filter having a red photoresist, a green photoresist and a blue photoresist, characterized by a spectrum. Some terms are defined as following:

a first spectrum of dark state $a(\lambda)$, which is measured for light emitted from a backlight through two polarizers when the color filter is disposed between the two polarizers with polarization directions orthogonal to each other;

a second spectrum of dark state $b(\lambda)$, which is measured for light emitted from the backlight through the two polarizers without the color filter disposed between the two polarizers;

a ratio spectrum of light leakage intensity $I(\lambda)$, which is defined as the ratio of the first spectrum of dark state to the second spectrum of dark state $(a(\lambda)/b(\lambda))$;

a first ratio of light leakage intensity $P_1$, which is the maximum value in a first wavelength region in the ratio spectrum of light leakage intensity, and the first wavelength region is corresponding to overlap between the ratio spectrum of light leakage intensity of a green photoresist and that of a blue photoresist;

a second ratio of light leakage intensity $P_2$, which is the maximum value in a second wavelength region in the ratio spectrum of light leakage intensity, and the second wavelength region is corresponding to the ratio spectrum of light leakage intensity of a red photoresist;

a first average value $P_{1,avg}$, which is obtained by averaging N1 number of ahead of the first ratio of light leakage intensity $P_1$, and N1 number of behind the first ratio of light leakage intensity $P_1$; and a second average value $P_{2,avg}$, which is obtained by averaging N2 number of ahead of the second ratio of light leakage intensity $P_2$, and N2 number of behind the second ratio of light leakage intensity $P_2$.

Characterized is that the color filter fits below conditions: $P_1<1$, $P_2<1$ and $0.74 \leq P_{1,avg}/P_{2,avg} \leq 2$.

The invention also provides a display panel including above color filter.

The invention provides a method for testing a color filter with a red, a green and a blue photoresists. The method comprises: disposing the color filter between two polarizers with polarization directions orthogonal to each other; providing a backlight under the polarizers; measuring a first spectrum of dark state $a(\lambda)$ on the polarizers; removing the color filter and measuring a second spectrum of dark state $b(\lambda)$ on the polarizers. The ratio of the first spectrum of dark state to the second spectrum of dark state $(a(\lambda)/b(\lambda))$ is defined as a ratio spectrum of light leakage intensity $I(\lambda)$.

Subsequently, the method further includes:

measuring a first ratio of light leakage intensity $P_1$, which is the maximum value in a first wavelength region in the ratio spectrum of light leakage intensity, and the first wavelength region is corresponding to overlap between the ratio spectrum of light leakage intensity of a green photoresist and that of a blue photoresist;

measuring a second ratio of light leakage intensity $P_2$, which is the maximum value in a second wavelength region in the ratio spectrum of light leakage intensity, and the second wavelength region is corresponding to the ratio spectrum of light leakage intensity of a red photoresist;

generating a first average ratio $P_{1,avg}$, which is obtained by averaging N1 number of ahead of the first ratio of light leakage intensity $P_1$, and N1 number of behind the first ratio of light leakage intensity $P_1$;

generating a second average value $P_{2,avg}$, which is obtained by averaging N2 number of ahead of the second ratio of light leakage intensity $P_2$, and N2 number of behind the second ratio of light leakage intensity $P_2$;

Finally, the color filter is checked if satisfying the following conditions: $P_1<1$, $P_2<1$ and $0.74 \leq P_{1,avg}/P_{2,avg} \leq 2$.

If the color filter matches the above conditions, it has features of low color shift and high contrast ratio.

BRIEF DESCRIPTION OF THE DRAWINGS

Table 1 and Table 2 are the data of testing color filters A-H.

DESCRIPTION OF THE PREFERRED EMBODIMENTS

The invention defines the light leakage spectrum of dark state to overcome the problem of color shift for color filter in the dark state. The light leakage spectrum of dark state is determined by spectrum analyzers or optical calorimeter to induce the ratio conditions about color filters.

When color filters meet above conditions or colors filters is manufactured by above conditions, they have features of low color shift in the dark state.

Figure 1A:
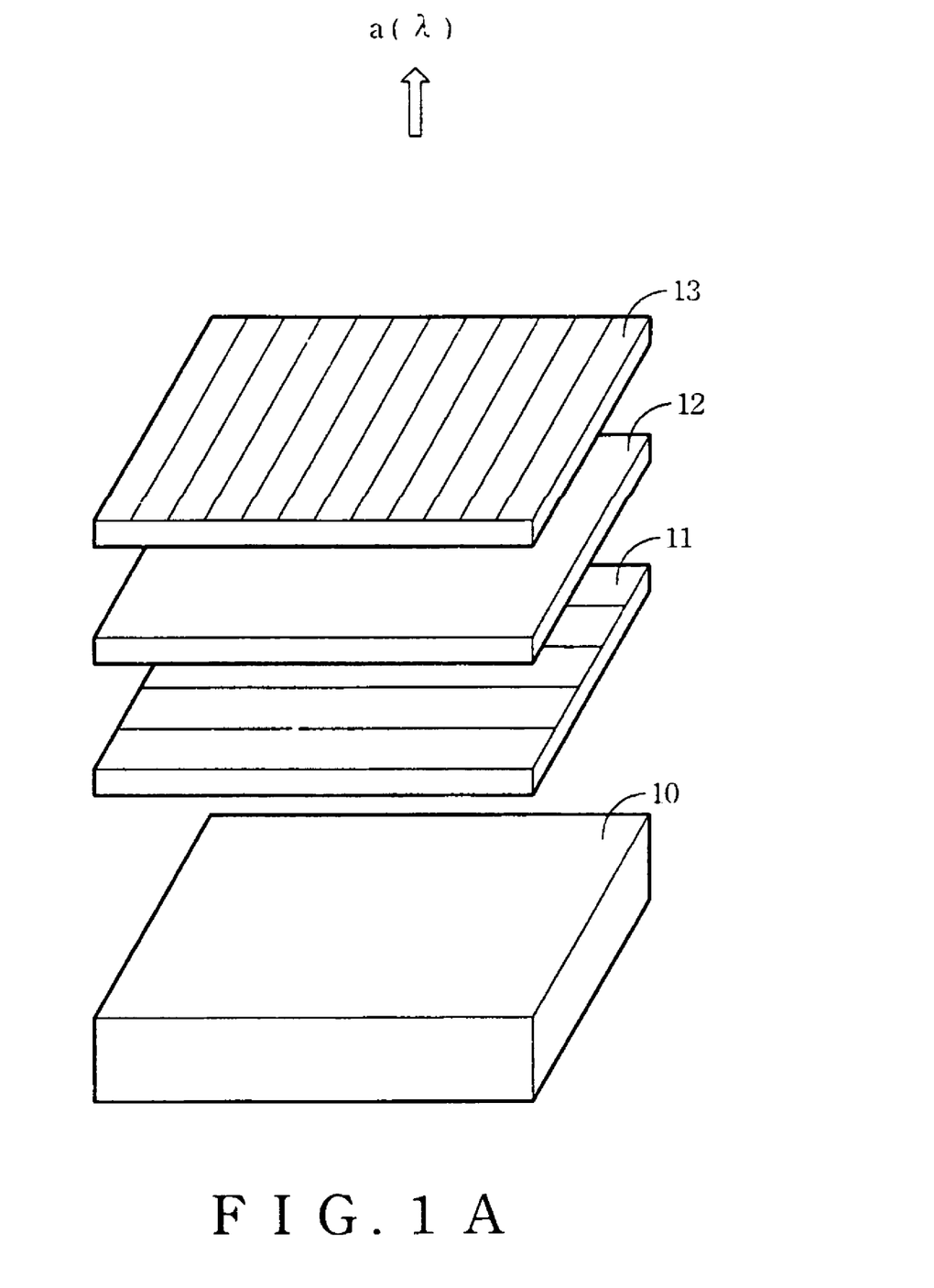
FIG. 1A is a sketch diagram to show a determination apparatus for measuring the first spectrum of dark state.

Below is the defined conditions of light leakage spectrum for color filter in dark state. Referring to FIG. 1A, it shows a sketch diagram of determination apparatus for measuring a first spectrum of dark state. The determination apparatus is used to measure the first spectrum of dark state $a(\lambda)$ of a color filter 12 which includes red, green and blue photoresists.

The first spectrum of dark state $a(\lambda)$ is measured for light emitted from a backlight 10 through two polarizers 11, 13 when the color filter 12 is sandwiched between the two polarizers 11, 13 with polarization directions orthogonal to each other.

Figure 1B:
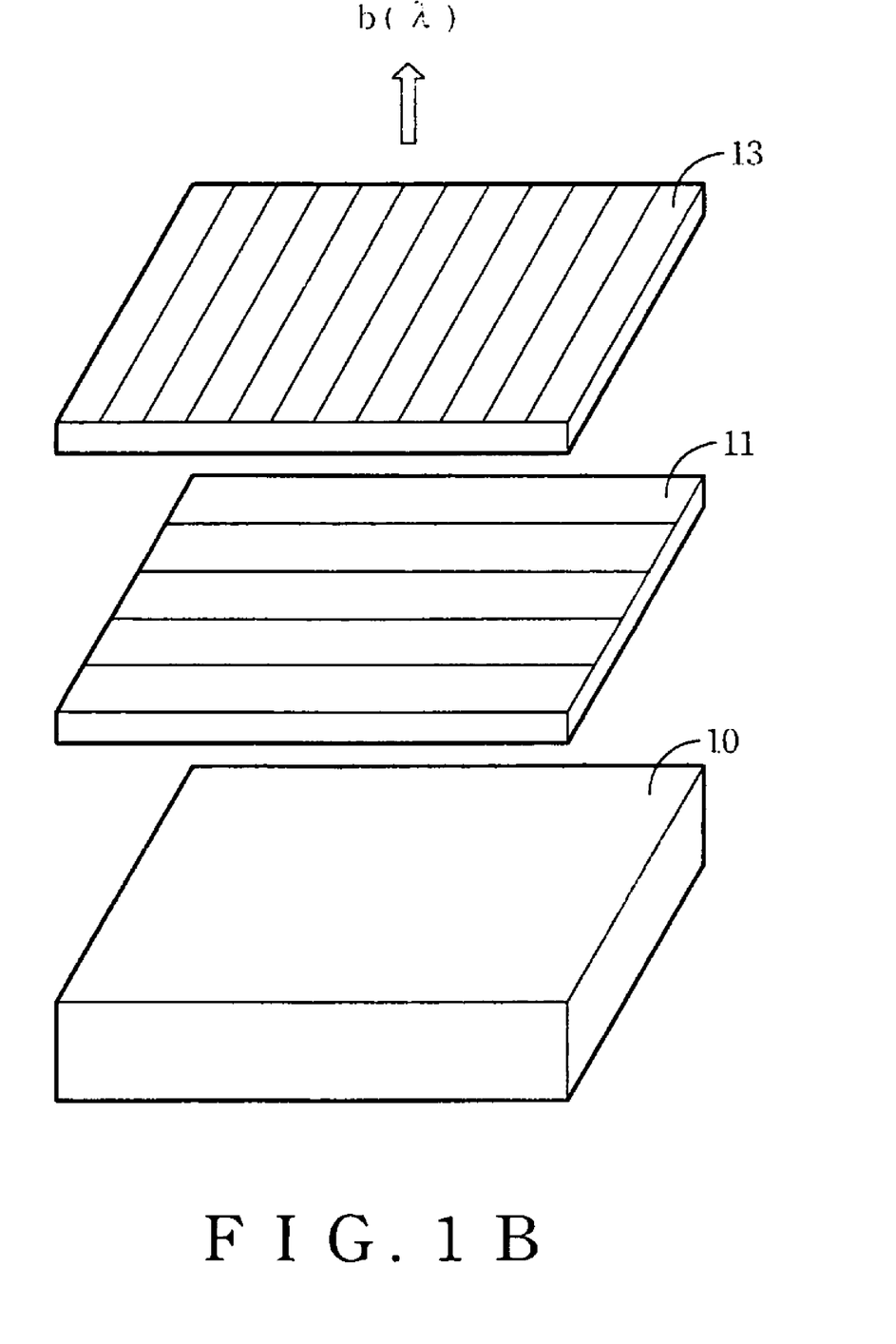
FIG. 1B is a sketch diagram to show a determination apparatus for measuring the second spectrum of dark state.

FIG. 1B is a sketch diagram of a determination apparatus for measuring a second spectrum of dark state. The determination apparatus is used to measured the spectrum of dark state when light emitted from the backlight through the two polarizers without the color filter sandwiched between the two polarizers 11, 13.

Namely, the second spectrum of dark state $b(\lambda)$ is measured for light emitted from the backlight 10 through the two polarizers 11, 13 when removing the color filter 12 of FIG. 1A.

Subsequently, a ratio spectrum of light leakage intensity $(a(\lambda)/b(\lambda))$ is defined as the ratio of the first spectrum of dark state $a(\lambda)$ to the second spectrum of dark state $b(\lambda)$.

Note that the conventional definition of proportion of the contrast ratio of photoresist is possible to be changed with backlight and polarizers. The above ratio of light leakage intensity is independent of the effect of backlight and polarizers, and is proper to the color filter. So the ratio of light leakage intensity is not changed with different backlight or polarizers.

Figure 2:
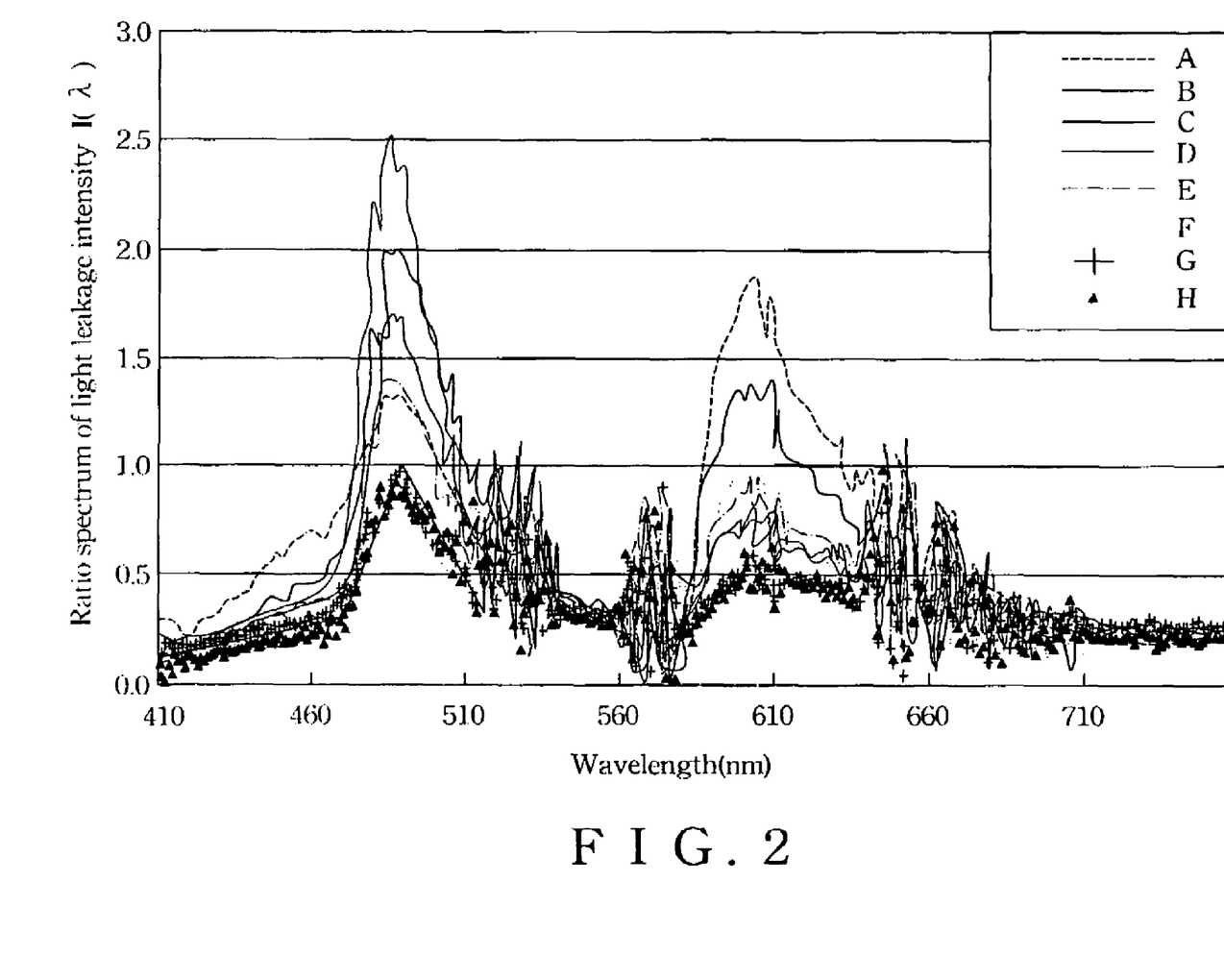
FIG. 2 is a ratio spectrum of light leakage intensity measured from several color filters.

FIG. 2 shows the ratio spectrum of light leakage intensity $I(\lambda)$ measured from eight color filters A to H. The abscissa represents the ratio spectrum of light leakage intensity, and the ordinate represents the wavelength range.

The wavelength range can be divided into a first wavelength region and a second wavelength region. The first wavelength region is corresponding to overlap between the ratio spectrum of light leakage intensity $I(\lambda)$ of the green photoresist and that of the blue, and preferred wavelength is 460-510 nm. The second wavelength region is corresponding to the ratio spectrum of light leakage intensity $I(\lambda)$ of the red photoresist, and preferred wavelength is 580-650 nm.

Each color filter has a first ratio of light leakage intensity $P_1$, which is defined as the maximum value in the first wavelength region in the ratio spectrum of light leakage intensity $I(\lambda)$. Each color filter has a second ratio of light leakage intensity $P_2$, which is defined as the maximum value in the second wavelength region in the ratio spectrum of light leakage intensity $I(\lambda)$.

Subsequently, a first average value $P_{1,avg}$ is obtained by averaging N1 number of ahead of the first ratio of light leakage intensity $P_1$, and N1 number of behind the first ratio of light leakage intensity $P_1$. A second average value $P_{2,avg}$ is obtained by averaging N2 number of ahead of the second ratio of light leakage intensity $P_2$, and N2 number of behind the second ratio of light leakage intensity $P_2$. Both $N1 \neq N2$ and $N1=N2$ are available, and preferred is $N1=N2=5$.

In another embodiment, the first average value $P_{1,avg}$ is obtained by averaging the ratios of light leakage intensity in the wavelength range leading and lagging the wavelength $\lambda_{1,max}$ corresponding to the first ratio of light leakage intensity $P_1$ by 1 nm. The second average value $P_{2,avg}$ is obtained by averaging the ratios of light leakage intensity in to the wavelength leading and lagging the wavelength $\lambda_{2,max}$ corresponding to the second ratio of light leakage intensity $P_2$ by 11 nm. An average value $P_{n,avg}$ is expressed as $$P_{n,avg} = \frac{\sum_{\lambda_{n,max}-5}^{\lambda_{n,max}+5} I(\lambda)}{11}.$$

According to the above measurement and data, when the color filter satisfy following conditions: $P_1<1$, $P_2<1$ and $0.74 \leq P_{1,avg}/P_{2,avg} \leq 2$, it has features of high contrast ratio and low color shift in the dark state.

However, when the two conditions are set up simultaneously, the color filter has features of high contrast ratio and low color shift. If the color filter only meets the condition of $0.74 \leq P_{1,avg}/P_{2,avg} \leq 2$, it only has the feature of low color shift of dark state.

Figure 3A:
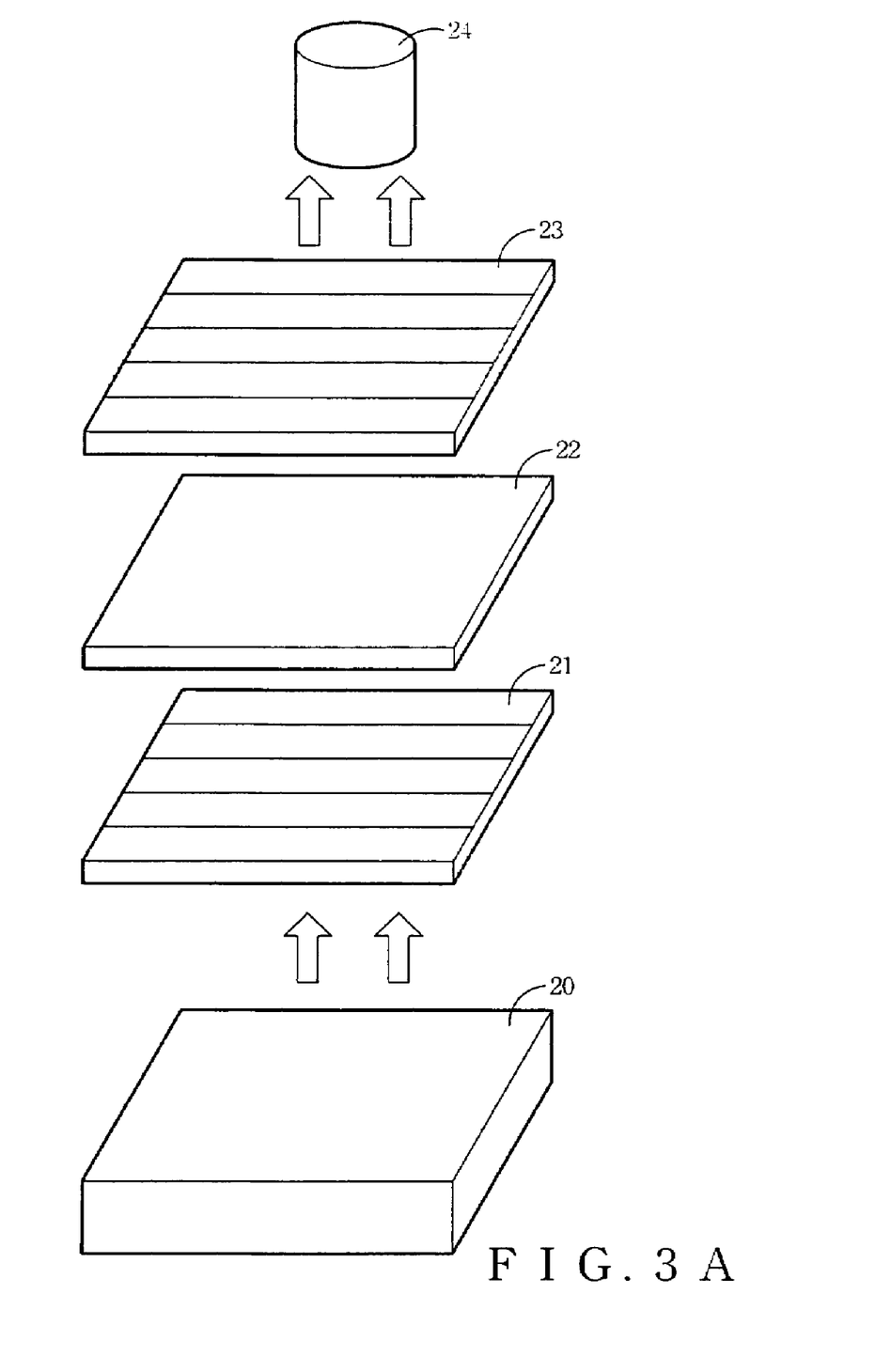
FIG. 3A is a sketch diagram of determination apparatus for testing the luminance and color coordinates in bright state for color filter in the present invention.
Figure 3B:
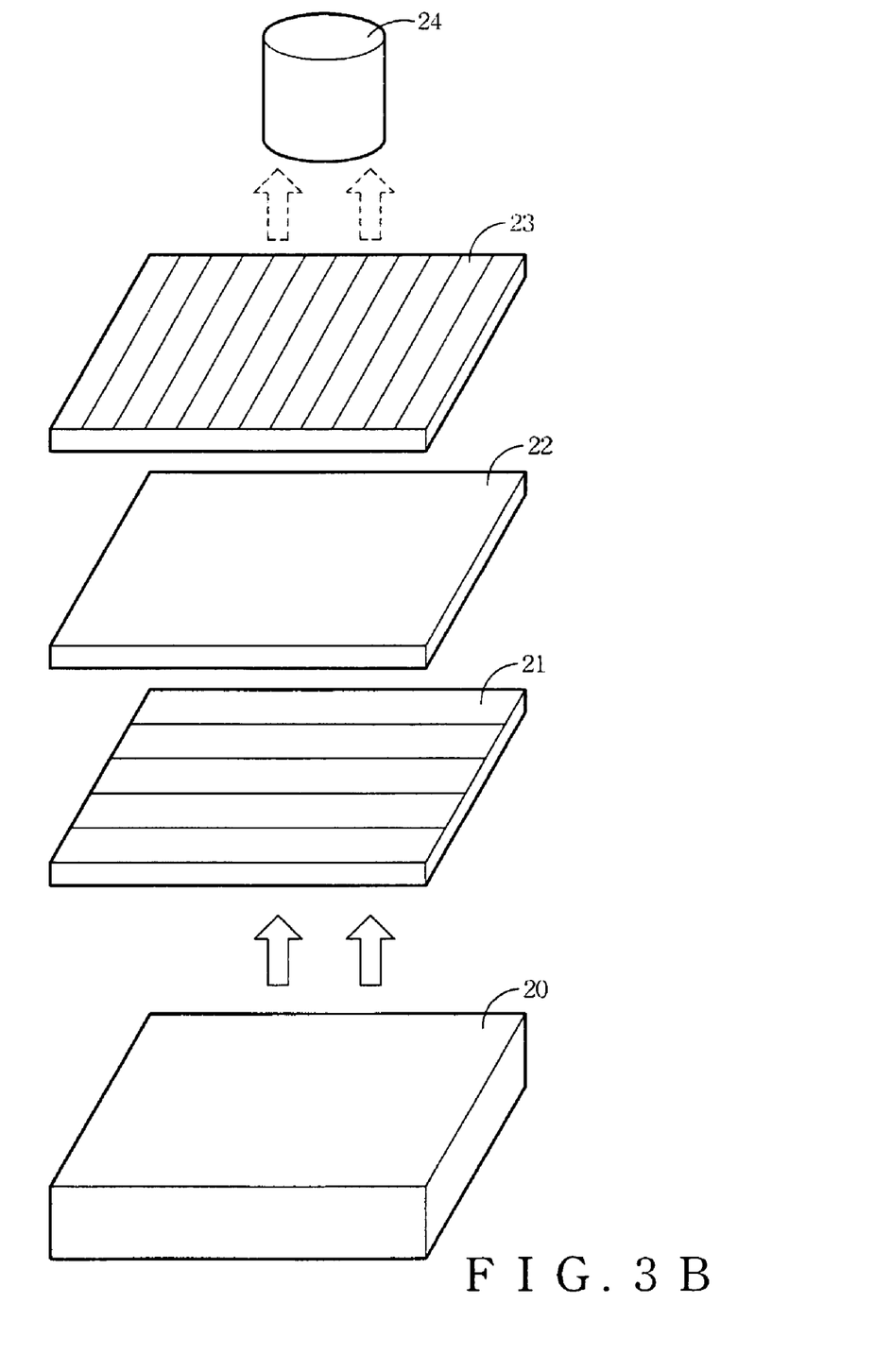
FIG. 3B is a sketch diagram of determination apparatus for testing the luminance and color coordinates in dark state for color filter in the present invention.

The contrast ratio and the color shift of dark state for color filter can be measured by following method. Referring to FIG. 3A and FIG. 3B, FIG. 3A is a sketch diagram of a determination apparatus for measuring luminance and color coordinates in bright state for the color filter of the invention. The apparatus includes a backlight 20, a polarizer 21, a color filter 22, a polarizer 23, and a detector 24 deposited in order. The color filter 22 is implemented between two polarizers 21, 23 with polarization directions parallel with each other. The backlight 20 is implemented under the two polarizers 21, 23, so that the detector 24 can detect data for the color filter 22 in bright state.

FIG. 3B is a sketch diagram of a determination apparatus for testing luminance and color coordinates for the color filter in dark state. The apparatus is disposed as FIG. 3A, however, the polarization directions of two polarizers are respectively orthogonal to each other. Namely, the color filter 22 is implemented between two polarizers with polarization directions orthogonal to each other. The backlight 20 is implemented under the two polarizers 21, 23, so that the detector 24 can detect data for the color filter 22 in the dark state.

However, if the color filter 22 matches the chromaticity radius $R=\sqrt{(x_p-x_c)^2+(y_p-y_c)^2} \leq 0.13$, then it has feature of low color shift in the dark state. Referring to FIG. 3A, where $(x_p, y_p)$ is a bright state color coordinates in response to the color filter 22 being disposed between the two polarizers 21, 23 with polarization directions parallel to each other, and the backlight 20 is applying under two polarizers 21, 23. U.S. Pat. No. 20050219443 is a cited reference regarding the chromaticity radius formula, but the invention is not limited to this formula.

Referring to FIG. 3B, where $(x_c, y_c)$ is a dark state color coordinates in response to the color filter 22 being disposed between the two polarizers 21, 23 with polarization directions orthogonal to each other, and the backlight 20 is applying under two polarizers 21, 23.

If the color filter has a contrast ratio larger than 8000, it is defined as a color filter with high contrast ratio. The contrast ratio is defined as a ratio of luminance of the color filter measured in the bright state to that measured in the dark state. The luminance can be measured by the determination apparatus shown in FIG. 3A and FIG. 3B.

Table 1 and Table 2 list data of the color coordinates measured in the bright state and in the dark state, contrast ratio, chromaticity radius and $P_{1,avg}/P_{2,avg}$ for eight color filters A to H.

In this embodiment, $P_{1,avg}/P_{2,avg}$ is obtained by N1=N2=5 in Table 1, and is obtained by N1≠N2(N1=3; N2=5) in Table 2.

If one of the eight color filter A-H matches $0.74 \leq P_{1,avg}/P_{2,avg} \leq 2$, then it matches low chromaticity radius $R = \sqrt{(x_p-x_c)^2+(y_p-y_c)^2} \leq 0.13$ in the dark state, referring to Table 1 and Table 2. Namely, if $0.74 \leq P_{1,avg}/P_{2,avg} \leq 2$, the color filter has feature of low color shift in the dark state.

In Table 1 and Table 2, six color filters A,B,E,F,G and H meet $0.74 \leq P_{1,avg}/P_{2,avg} \leq 2$, and meet $R = \sqrt{(x_p-x_c)^2+(y_p-y_c)^2} \leq 0.13$, so that they have feature of low color shift in the dark state. Color filters G and H have both features of low color shift and high contrast ratio.

Note that whether N1=N2 or N1≠N2, the $P_{1,avg}/P_{2,avg}$ can meet the conditions of $R=\sqrt{(x_p-x_c)^2+(y_p-y_c)^2} \leq 0.13$ and $0.74 \leq P_{1,avg}/P_{2,avg} \leq 2$. The above conditions are all available whether the color filter has high contrast ratio (>8000) or low contrast ratio (<8000). In addition, the color filter has high contrast ratio (>8000) if both the first ratio of light leakage intensity $P_1$ and the second intensity ratio of light leakage $P_2$ are smaller than 1 ($P_1<1$, $P_2<1$). Referring to Table 1 and Table 2, both the first ratio of light leakage intensity $P_1$ and the second ratio of light leakage intensity $P_2$ of color filters G and H are smaller than 1($P_1<1$, $P_2<1$), and color filters G and H meet the condition of $0.74 \leq P_{1,avg}/P_{2,avg} \leq 2$. Therefore, both color filters G and H have features of low color shift in the dark state and high contrast ratio.

Figure 4:
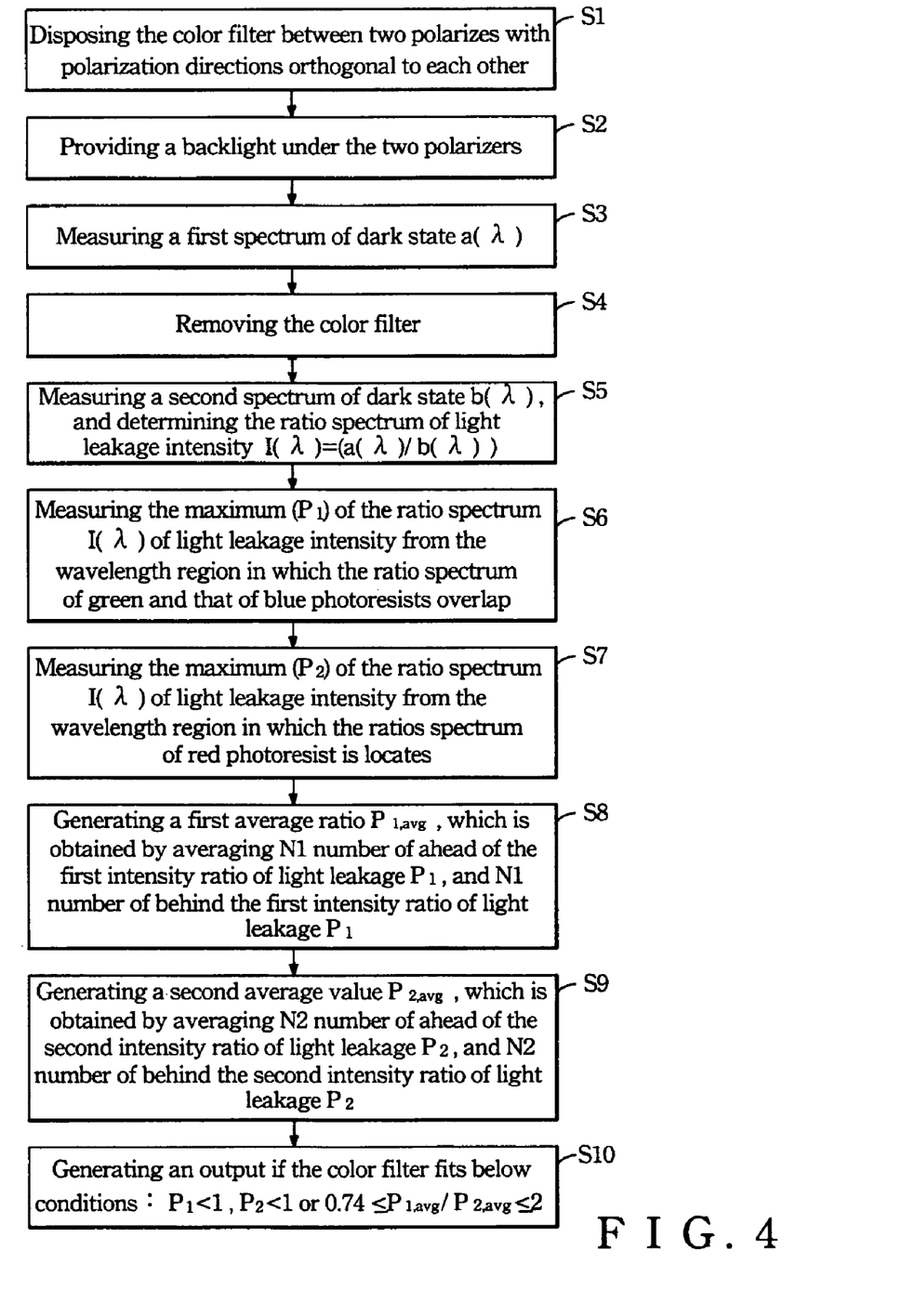
FIG. 4 is a flow chart of the testing method for the color filter of the present invention.

Referring to FIG. 4, according to above conditions, the invention provides a method for testing the color filter. The method includes the following steps: disposing the color filter between two polarizers with polarization directions orthogonal to each other (S1); providing a backlight under the polarizers (S2); measuring a first spectrum of dark state a(λ) on the polarizers (S3); removing the color filter (S4); measuring a second spectrum of dark state b(λ) on the polarizers; subsequently, determining the ratio spectrum of light leakage intensity I(λ), which is the ratio of the first and the second spectrum of dark state (a(λ)/b(λ))(S5).

Next step is, to measure a first ratio of light leakage intensity $P_1$ which is the maximum value in the first wavelength region in the ratio spectrum of light leakage intensity I(λ). The first wavelength region is corresponding to overlap between the ratio spectrum of light leakage intensity of the green photoresist and that of the blue photoresist. (S6)

A second ratio of light leakage intensity $P_2$ is measured, and defined as the maximum value in the second wavelength region in the ratio spectrum of light leakage intensity. The second wavelength region is corresponding to the ratio spectrum of light leakage intensity of the red photoresist. (S7) It is not limited the step 6 and the step 7 in order.

The step 8 is to generate a first average ratio $P_{1,avg}$ (S8), which is obtained by averaging N1 number of ahead of the first intensity ratio of light leakage $P_1$, and N1 number of behind the first intensity ratio of light leakage $P_1$. Step 9 is to generate a second average value $P_{2,avg}$, which is obtained by averaging N2 number of ahead of the second intensity ratio of light leakage $P_2$, and N2 number of behind the second intensity ratio of light leakage $P_2$.

The last step is to generate an output if the color filter fits below conditions: P1<1, P2<1 and $0.74 \leq P_{1,avg}/P_{2,avg} \leq 2$. (S10)

The invention has advantages as follows:

A. The conditions do not be changed with the polarizers and backlight because they are defined by the light leakage spectrum in the dark state.
B. The conditions can be applied to the color filters with high or low contrast ratios to overcome color shift.
C. The conditions can be used to select the color filter with low color shift and high contrast ratio.

While the preferred embodiments of the present invention have been set forth for the purpose of disclosure, modifications of the disclosed embodiments of the present invention as well as other embodiments thereof may occur to those skilled in the art. Accordingly, the appended claims are intended to cover all embodiments which do not depart from the spirit and scope of the present invention.

What is claimed is:

1. A color filter having a red photoresist, a green photoresist and a blue photoresist, and having characteristics defined by following terms:
   a first spectrum of dark state a(λ), which is measured for light emitted from a backlight through two polarizers when the color filter is disposed between the two polarizers with polarization directions orthogonal to each other;
   a second spectrum of dark state b(λ), which is measured for light emitted from the backlight through the two polarizers without the color filter disposed between the two polarizers;
   a ratio spectrum of light leakage intensity I(λ), which is defined as the ratio of the first spectrum of dark state to the second spectrum of dark state (a(λ)/b(λ));
   a first ratio of light leakage intensity $P_1$, which is the maximum value in a first wavelength region in the ratio spectrum of light leakage intensity I(λ), wherein the first wavelength region is corresponding to overlap between the ratio spectrum of light leakage intensity of a green photoresist and that of a blue photoresist;
   a second ratio of light leakage intensity $P_2$, which is the maximum value in a second wavelength region in the ratio spectrum of light leakage intensity I(λ), wherein the second wavelength region is corresponding to the ratio spectrum of light leakage intensity of a red photoresist;
   a first average value $P_{1,avg}$, which is obtained by averaging N1 number of ahead of the first ratio of light leakage intensity $P_1$ and N1 number of behind the first ratio of light leakage intensity $P_1$; and
   a second average value $P_{2,avg}$, which is obtained by averaging N2 number of ahead of the second ratio of light leakage intensity $P_2$ and N2 number of behind the second ratio of light leakage intensity $P_2$;
   characterized in that, the color filter satisfying below conditions: $P_1<1$, $P_2<1$ and $0.74 \leq P_{1,avg}/P_{2,avg} \leq 2$.

2. The color filter of claim 1, wherein N1≠N2.

3. The color filter of claim 1, wherein N1=N2=5.

4. The color filter of claim 1, wherein the first average value $P_{1,avg}$ is obtained by averaging the ratios of light leakage intensity, which correspond to the wavelength range leading and lagging the wavelength $\lambda_{1,max}$ corresponding to the first ratio of light leakage intensity $P_1$ by 11 nm; and the second average value $P_{2,avg}$ is obtained by averaging the ratios of light leakage intensity, which correspond to the wavelength leading and lagging the wavelength $\lambda_{2,max}$ corresponding to the second ratio of light leakage intensity $P_2$ by 11 nm; and an average value $P_{n,avg}$ is expressed as $$P_{n,avg} = \frac{\sum_{\lambda_{n,max}-5}^{\lambda_{n,max}+5} I(\lambda)}{11}.$$

5. The color filter of claim 1, wherein the first wavelength region locates between 460 nm and 510 nm, and the second wavelength region locates between 580 nm and 650 nm.

6. The color filter of claim 1, further having characteristics defined by a chromaticity radius $R = \sqrt{(x_p-x_c)^2+(y_p-y_c)^2} \leq 0.13$, wherein $(x_p,y_p)$ is a bright state color coordinates in response to the color filter being disposed between the two polarizers with polarization directions parallel to each other, and the backlight is applying under two polarizers; wherein $(x_c,y_c)$ is a dark state color coordinates in response to the color filter being disposed between the two polarizers with polarization directions orthogonal to each other, and the backlight is applying under two polarizers.

7. The color filter of claim 1, further having characteristics defined by a contrast ratio larger than 8000, wherein the contrast ratio is defined as a ratio of luminance of the color filter measured in the bright state to that measured in the dark state.

8. A method for testing a color filter with a red, a green and a blue photoresists, comprising:
disposing the color filter between two polarizers with polarization directions orthogonal to each other;
providing a backlight under the polarizers;
measuring a first spectrum of dark state $a(\lambda)$ on the polarizers;
removing the color filter;
measuring a second spectrum of dark state $b(\lambda)$ on the polarizers, wherein a ratio spectrum of light leakage intensity $I(\lambda)$ is the ratio of the first and the second spectrum of dark state $(a(\lambda)/b(\lambda))$;
measuring a first ratio of light leakage intensity $P_1$, which is the maximum value in a first wavelength region in the ratio spectrum of light leakage intensity $I(\lambda)$, wherein the first wavelength region is corresponding to overlap between and the ratio spectrum of light leakage intensity of a green photoresist and that of a blue photoresist;
measuring a second ratio of light leakage intensity $P_2$, which is the maximum value in a second wavelength region in the ratio spectrum of light leakage intensity $I(\lambda)$, wherein the second wavelength region is corresponding to the ratio spectrum of light leakage intensity of a red photoresist;
generating a first average ratio $P_{1,avg}$, which is obtained by averaging N1 number of ahead of the first ratio of light leakage intensity $P_1$ and N1 number of behind the first ratio of light leakage intensity $P_1$;
generating a second average value $P_{2,avg}$, which is obtained by averaging N2 number of ahead of the second ratio of light leakage intensity $P_2$ and N2 number of behind the second ratio of light leakage intensity $P_2$; and
generating an output if the color filter satisfies the following conditions: $P_1 < 1$, $P_2 < 1$ 且 $0.74 \leq P_{1,avg}/P_{2,avg} \leq 2$.

9. The method of claim 8, wherein N1≠N2.

10. The method of claim 8, further comprising:
measuring five ratios ahead of the first ratio of light leakage intensity $P_1$ and five ratios behind the first ratio of light leakage intensity $P_1$ before generating the first average ratio $P_{1,avg}$; and
measuring five ratios ahead of the second ratio of light leakage intensity $P_2$ and five ratios behind the second ratio of light leakage intensity $P_2$ before generating the second average ratio $P_{2,avg}$.

11. The method of claim 8, further comprising:
measuring the ratios of light leakage intensity in the wavelength range leading and lagging the wavelength $\lambda_{1,max}$ corresponding to the first ratio of light leakage intensity $P_1$ by 11 nm before generating the first average ratio $P_{1,avg}$; and
measuring the ratios of light leakage intensity in the wavelength range leading and lagging the wavelength $\lambda_{2,max}$ corresponding to the second ratio of light leakage intensity $P_2$ by 11 nm before generating the second average ratio $P_{2,avg}$.

12. The method of claim 8, wherein the first wavelength region locates between 460 nm and 510 nm, and the second wavelength region locates between 580 nm and 650 nm.

13. A display panel comprising the color filter of claim 1.

14. The display of claim 13, wherein N1≠N2.

15. The display of claim 13, wherein N1=N2=5.

16. The display of claim 13, wherein the first average value $P_{1,avg}$ is obtained by averaging the ratios of light leakage intensity, which correspond to the wavelength range leading and lagging the wavelength $\lambda_{1,max}$ corresponding to the first ratio of light leakage intensity $P_1$ by 11 nm; and the second average value $P_{2,avg}$ is obtained by averaging the ratios of light leakage intensity, which correspond to the wavelength leading and lagging the wavelength $\lambda_{2,max}$ corresponding to the second ratio of light leakage intensity $P_2$ by 11 nm; and an average value $P_{n,avg}$ is expressed as $$P_{n,avg} = \frac{\sum_{\lambda_{n,max}-5}^{\lambda_{n,max}+5} I(\lambda)}{11}.$$

17. The display of claim 13, wherein the first wavelength region locates between 460 nm and 510 nm, and the second wavelength region locates between 580 nm and 650 nm.

18. The display of claim 13, wherein the color filter further has characteristics defined by a chromaticity radius $R = \sqrt{(x_p-x_c)^2+(y_p-y_c)^2} \leq 0.13$, wherein $(x_p,y_p)$ is a bright state color coordinates in response to the color filter being disposed between the two polarizers with polarization directions parallel to each other, and the backlight is applying under two polarizers; wherein $(x_c,y_c)$ is a dark state color coordinates in response to the color filter being disposed between the two polarizers with polarization directions orthogonal to each other, and the backlight is applying under two polarizers.

19. The color filter of claim 13, wherein the color filter further has characteristics defined by a contrast ratio larger than 8000, wherein the contrast ratio is defined as a ratio of luminance of the color filter measured in the bright state to that measured in the dark state.

* * * * *